United States Patent
Pontiroli et al.

(10) Patent No.: US 6,828,445 B2
(45) Date of Patent: Dec. 7, 2004

(54) PROCESS FOR THE PREPARATION OF BACCATIN III DERIVATIVES

(75) Inventors: Alessandro Pontiroli, Milan (IT); Ezio Bombardelli, Milan (IT)

(73) Assignee: Indena S.p.A., Milan (IT)

(*) Notice: Subject to any disclaimer, the term of this patent is extended or adjusted under 35 U.S.C. 154(b) by 0 days.

(21) Appl. No.: 10/343,991

(22) PCT Filed: Jul. 27, 2001

(86) PCT No.: PCT/EP01/08730

§ 371 (c)(1),
(2), (4) Date: Feb. 6, 2003

(87) PCT Pub. No.: WO02/12215

PCT Pub. Date: Feb. 14, 2002

(65) Prior Publication Data

US 2004/0014998 A1 Jan. 22, 2004

(30) Foreign Application Priority Data

Aug. 10, 2000 (IT) ..................................... MI2000A1869

(51) Int. Cl.$^7$ ............................................... C07D 317/70
(52) U.S. Cl. ....................................................... 549/229
(58) Field of Search ........................................ 549/229

(56) References Cited

U.S. PATENT DOCUMENTS

| 5,698,712 A | 12/1997 | Bombardelli et al. |
| 5,750,562 A | 5/1998 | Bombardelli et al. |

FOREIGN PATENT DOCUMENTS

| WO | WO 96 36622 | 11/1996 |
| WO | WO 00 52003 | 9/2000 |

*Primary Examiner*—Laura L. Stockton
(74) *Attorney, Agent, or Firm*—Young & Thompson

(57) ABSTRACT

A process for the preparation of 14β-hydroxy-1,4-carbonate-deacetylbaccatin III and intermediates useful for the preparation of novel taxan derivatives with antitumor activity are disclosed.

7 Claims, No Drawings

PROCESS FOR THE PREPARATION OF BACCATIN III DERIVATIVES

The present invention relates to novel intermediates useful in the synthesis of 14β-hydroxy-1,14-carbonate-deacetylbaccatin III derivatives, and to a process for the preparation thereof. The intermediates obtained with the process of the invention can be used in the preparation of novel taxan derivatives with antitumor activity.

Taxanes are one of the most important classes of antitumor agents developed in recent years. Paclitaxel is a complex diterpene isolated from the bark of *Taxus brevifolia* and is considered a "lead compound" for cancer therapy. Extensive research is at present being carried out for taxan derivatives having higher pharmacological activity and improved pharmacokinetic profile. A particular approach relates to the baccatin III derivatives variously modified with respect to the basic structure. Examples of said compounds are the 14β-hydroxy baccatin III derivatives disclosed in U.S. Pat. No. 5,705,508, WO 97/43291, WO 96/36622. At present, 14β-hydroxy-1,14-carbonate-deacetylbaccatin III derivatives are prepared starting from the 14β-hydroxy-deacetylbaccatin III precursor, which is a natural compound obtainable in small amounts by extraction of leaves of *Taxus wallichiana*, as disclosed in EP 559,019. There is strong need for novel intermediates or alternative processes to those commonly used, which allow to prepare 14β-hydroxy-1,14-carbonate-deacetylbaccatin III derivatives simply and effectively.

It has now been found that 14β-hydroxy-1,14-carbonate-deacetylbaccatin III can be prepared by means of a process using 10-deacetylbaccatin III as starting compound which, contrary to 14β-hydroxy-baccatin III, can be easily isolated in large amounts form *Taxus baccata* leaves.

Therefore, the present invention provides a process for the preparation of 14β-hydroxy-1,14-carbonate-deacetylbaccatin III comprising the following steps:

1. protection of the hydroxy groups at the positions 7 and 10 of 10 deacetylbaccatin III:

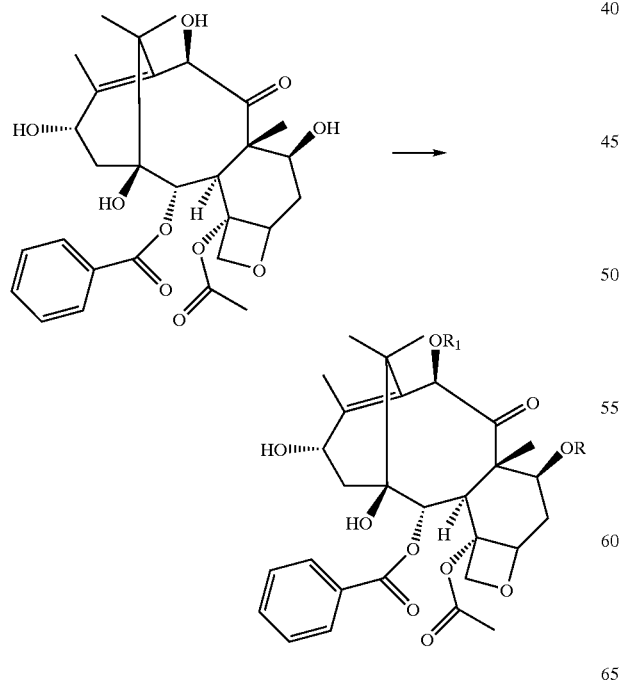

wherein R and $R_1$ are selected from hydrogen, $C_1$–$C_{10}$ alkyl or aryl, $C_1$–$C_{10}$ alkyl- or aryl-carbonyl, trichloroacetyl, $C_1$–$C_4$ trialkylsilyl; preferably, when R and $R_1$ are the same, they are trichloroacetyl, whereas when they are different, preferably R is trichloroacetyl and $R_1$ is acetyl, or R is triethyl or trimethylsilyl and $R_1$ is acetyl;

2. two-step oxidation to give the derivative oxidised at the 13-position and hydroxylated at the 14-position:

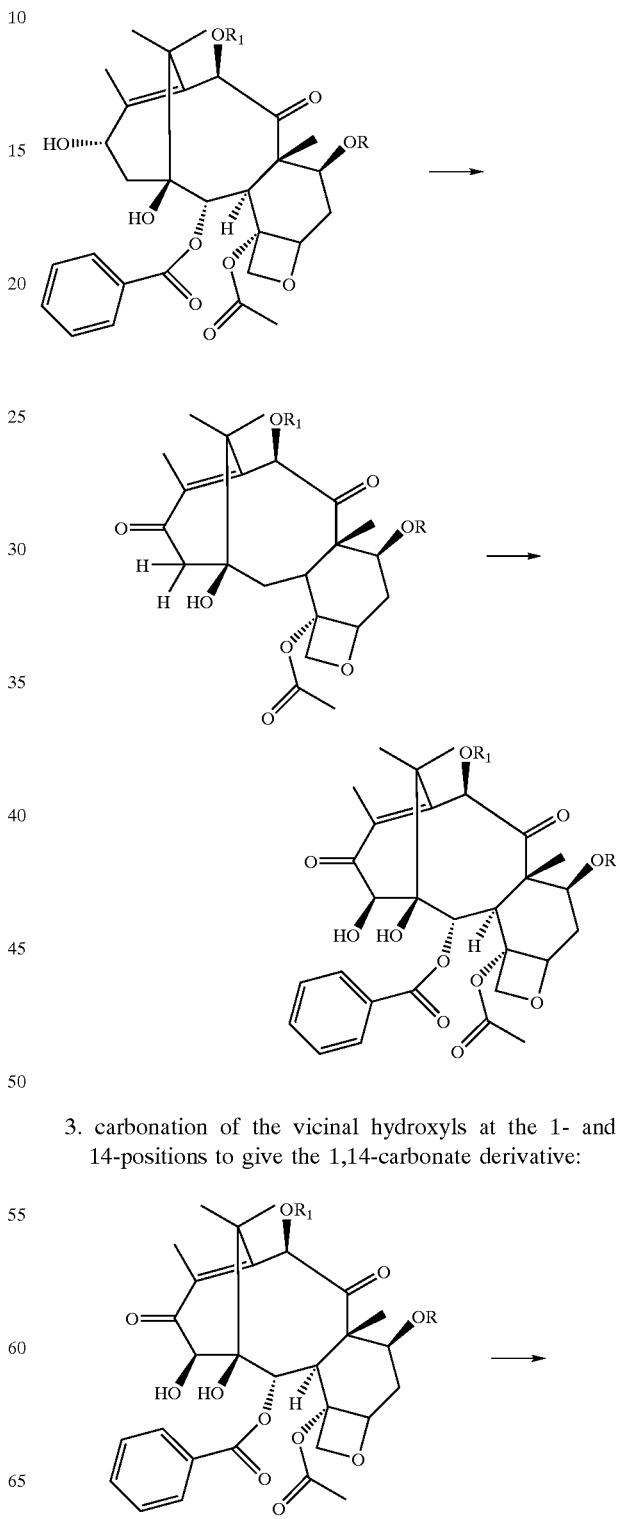

3. carbonation of the vicinal hydroxyls at the 1- and 14-positions to give the 1,14-carbonate derivative:

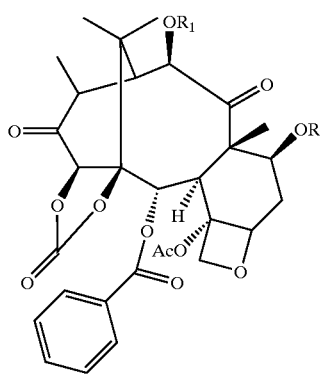

4. reduction of the carbonyl at the 13-position:

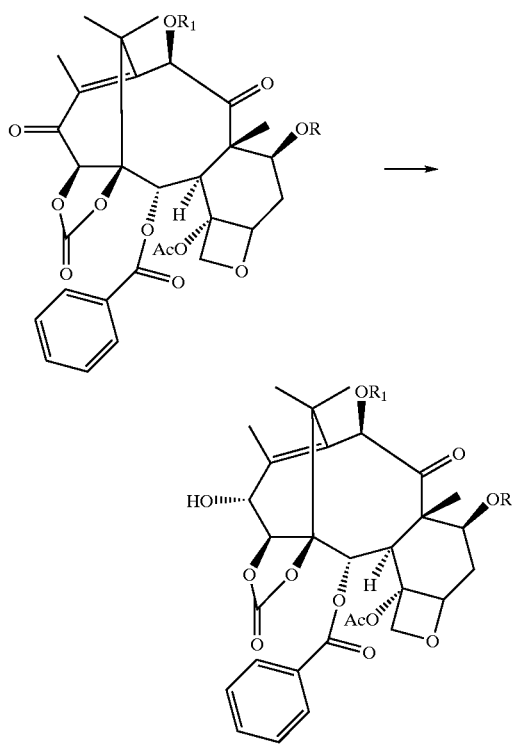

5. removal of the protective groups at the 7- and 10-positions:

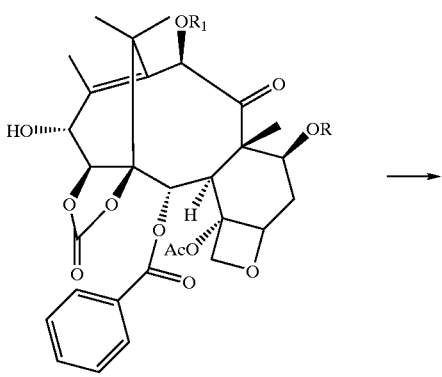

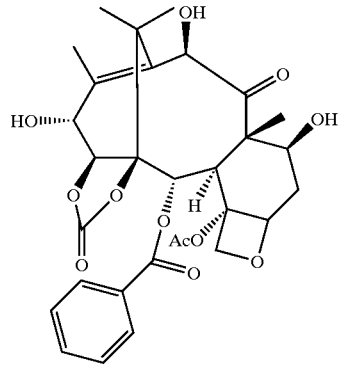

The procedures for the protection of the 7- and 10-hydroxyls are described by Holton et al., Tetrahedron Letters 39, (1998) 2883–2886. The selective protection of the hydroxyls of the starting compound deacetylbaccatin III is possible due to their different reactivity. In particular, the reactivity towards acylating, alkylating or silylating agents has been found to vary in the order C(7)—OH>C(10)—OH>C(13)—OH>C(1)—OH, therefore the groups at 7- and 10-can be selectively protected while keeping the hydroxyls at 1- and 13-free. Furthermore, by changing the reaction conditions, it is possible to reverse the reactivity order of the hydroxyls at 7- and 10-thus allowing the differential substitution thereof. Examples of reactants and reaction conditions usable in the protection of the hydroxyls at 10- and 7- are reported in the above cited publication.

The oxidation step of the hydroxyl at the 13-position is achieved with manganese dioxide or bismuth dioxide in a solvent selected from acetonitrile, acetone or ethyl acetate/methylene chloride 9:1 mixtures, under vigorous stirring, preferably with manganese dioxide in acetonitrile or acetone. The reaction proceeds quickly to give the oxidised derivative at the 13-position, which can be recovered from the reaction medium, whereas a longer reaction yields the 13-oxidised and 14-hydroxylated derivative.

The subsequent carbonation step of the hydroxyls at the 1- and 14-positions is usually effected with phosgene or triphosgene in a methylene chloride/toluene mixture in the presence of pyridine. Subsequently, the resulting 1,14-carbonate derivative can be easily reduced at the 13-position to give the corresponding 13-hydroxy derivative. Said reduction takes place regioselectively on the carbonyl at 13-while the carbonyl at 9-remains unchanged, and stereoselectively, affording almost exclusively the 13-α isomer. This reaction is usually carried out with sodium borohydride in methanol and provides high yields. The last step consists in deprotecting the hydroxyls at the 7- and 10-positions to give the final product 14β-hydroxy-1,14-carbonate deacetylbaccatin III. The conditions and the reactants which can be used in the selective deprotection of the hydroxyls at 7- and 10- are described in Zheng et al., Tetrahedron Lett., 1995, 36, 2001, and in Datta et al., J. Org. Chem., 1995, 60, 761. The resulting final product is an extremely useful intermediate for the synthesis of a variety of taxan derivatives. As mentioned above, said intermediate was prepared until now starting from 14β-hydroxy baccatin III extracted from the leaves of *Taxus wallichiana* in low yields. The process of the present invention allows to prepare the same intermediate in high yields starting from a compound available in large amounts. Examples of compounds with antitumor activity which can be prepared starting from 14β-hydroxy-1,14-carbonate deacetylbaccatin III are reported in U.S. Pat. No. 5,705,508, WO 97/43291, WO 96/36622.

According to a preferred embodiment of the process of the invention, deacetylbaccatin III is reacted with trichloroacetyl chloride in methylene chloride in the presence of triethylamine and using N,N-dimethylaminopyridine (DMAP) in catalytic amounts. The use of trichloroacetate as protecting group proved to be very advantageous in the oxidation, carbonation and reduction steps according to the process of the invention. In particular, the 7,10-bis-trichloroacetate derivative, which is obtained in quantitative yields from the starting compound, after oxidation and carbonation is easily reduced at the 13-position with simultaneous deprotection of the trichloroacetic groups to give 14β-hydroxy-1,14-carbonate-deacetylbaccatin III. The use of DMAP in catalytic amounts provides definite advantages from the industrial and environmental point of views, when considering that until now the acylations of this substrate were carried out in pyridine with consequent discharge problems of the residual solvent.

The following intermediates obtained according to the preferred embodiment described above are part of the present invention:

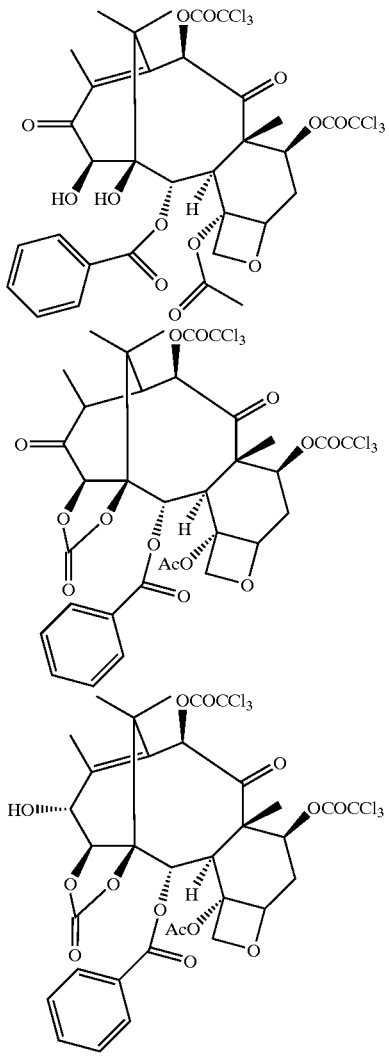

The following examples illustrate the invention in greater detail.

EXAMPLE I

Preparation of 7,10-bistrichloroacetyl-10-deacetylbaccatin III

First Alternative 4.77 ml of trichloroacetic anhydride (42.32 mmol) is added by drops to a solution of 10 g of 10-deacetylbaccatin III (18.4 mmol) in 125 ml of dry methylene chloride and 42 ml of pyridine. The reaction mixture is kept under stirring for three hours or anyway until completion of the reaction, checking by TLC on silica gel using as eluent an n-hexane/ethyl acetate 1:1 mixture. After completion of the reaction, 5 ml of methanol are added to destroy the excess of trichloroacetic anhydride, then water is added. The organic phase is thoroughly washed with acidic water (HCl) to remove pyridine, whereas the remaining organic phase is dried over MgSO4 and concentrated to dryness under vacuum, to obtain a pale yellow solid (17 g) which is crystallised from chloroform:

$[\alpha]_D$ –34° ($CH_2Cl_2$ C5.8) IR (KBr) 3517, 1771, 1728, 1240, 981, 819, 787, 675 $cm^{-1}$;

$^1$H-NMR (200 MH): δ 8.11 (Bz C), 7.46 (Bz, BB'), 6.50 (s, H-10), 5.72 (m, H-7 H-29, 5.02 (d, J=8 Hz, H-5), 4.95 8 m, H-13), 4.37 (d, J=8 Hz, H-20a), 4.18 (d, J=8 Hz, H-20b), 4.02 (d, J=6 Hz, H-3), 2.32 (s, 4-Ac), 2.22 (s, H-1.8), 1.91 (s, H-19), 1.25 and 1.11 (s, H-16, H-17), 1.94 (m, H 14α), 1.89 (m, H14β).

Second Alternative:

10-deacetylbaccatin III (10 g, 18.38 mmol) is suspended in $CH_2Cl_2$ (120 ml), added with DMAP (220 mg, 1.4 mmol, 0.1 eqv.) and cooled to 0° C. on ice bath. $Et_3N$ (10.26 ml, 73.6 mmol, 4 eqv.) and immediately after, $Cl_3CCOCl$ (4.12 ml, 36.8 mmol, 2 eqv.) are added under nitrogen stream in 5 min, keeping the temperature under 10° C. After completion of the addition, the mixture is left under stirring on ice bath for 15 min, then the bath is removed and the reaction stirred at room temperature for 1 h. After 1 h the reaction is checked by TLC (AcOEt 2/n-hexane 3, Rf 10-DAB III= 0.05, Rf 7,10-bistrichloroacetyl-10-DAB III=0,26) and added with $Cl_3CCOCl$ (1 ml, 0.5 eqv.). Stirring is continued at r.t. for 10 min, then the reaction is poured into a beaker containing 160 g of triturated ice and left under stirring until equilibrium at r.t. (about 1 h). The aqueous phase is then separated and extracted with $CH_2Cl_2$ (3×40 ml). The combined organic phases are washed with 1N HCl (20 ml), then with a $NaHCO_3$ saturated solution (20 ml), dried over $Na_2SO_4$ and the solvent is evaporated off. Crude weight: 16.5 g. After crystallisation from chloroform, the IR, $^1$H-NMR and $[\alpha]_D$ spectra are consistent with those of the compound obtained using pyridine and trichloroacetic anhydride.

EXAMPLE II

Oxidation at 13- and Hydroxylation at 14- of 7,10-bistrichloroacetate 10-deacetylbaccatin III 30 g of activated $MnO_2$ are added to a solution of 10-deacetylbaccatin III 7,10-bistrichloroacetate (3 g) in acetonitrile (40 ml), stirring the suspension with magnetic stirrer at room temperature and monitoring the progress of the reaction by TLC (petroleum ether-ethyl acetate 5:5; Rf of the starting material about 0.31). After about one hour, the formation of the 13-dehydroderivative is completed (TLC analysis, Rf of the 13-dehydroderivative about 0.50). Stirring is then continued for about 72 hours, during which time the 13-dehydroderivative is slowly oxidised to the corresponding 14β-hydroxy derivative (Rf about 0.36). The reaction mixture is filtered through Celite, and the cake is repeatedly washed with ethyl acetate. The solvent is evaporated off and the residue is purified by column chromatography on silica gel (100 ml, eluent petroleum ether-ethyl acetate 7:3) to obtain 170 mg of the 13-dehydroderivative and 2.38 g of the 14β-hydroxy-13-dehydroderivative.

13-dehydro-14β-hydroxy-10-deacetylbaccatin, 7,10-bistrichloroacetate: white powder, m.p. 97° C.; IR (KBr disc): 3440, 1780, 1767, 1736, 1686, 1267, 1232, 1103, 1010, 854 cm$^{-1}$;

$^1$H-NMR (200 MHz, CDCl$_3$): δ 8.07 (Bz AA'), 7.60 (Bz, C), 7.49 (Bz, BB'), 6.52 (s, H-10), 5.92 (d, J=6.7 Hz, H-2), 5.70 (br t, J=8.0 Hz, H-7), 4.95 (br d, J=8.2 Hz, H-5), 4.37 (d, J=8.2 Hz, H-20a), 4.31 (d, J=8.2 Hz, H-20b), 4.17 (s, H14), 4.02 (d, J=6.7 Hz, H-3), 2.71 (m, H-6), 2.29 (s, OAc), 2.17 (s, OAc), 1.96 (s, H-18), 1.27, 1.01 (s, H-16, H-17 and H-19).

EXAMPLE III
Oxidation/hydroxylation of 7-triethylsilylbaccatin III 10 g of activated MnO$_2$ are added to a solution of 7-triethylsilylbaccatin III (1.0 g) in acetonitrile (10 ml), stirring the suspension with magnetic stirrer at room temperature and monitoring the progress of the reaction by TLC (petroleum ether-ethyl acetate 6:4; Rf of the starting material about 0.25). After about two hours, the formation of the 13-dehydroderivative is completed (TLC analysis, Rf of the 13-dehydroderivative, about 0.45). Stirring is then continued for about 188 hours, during which time. further MnO$_2$ (10 g) is added. The 13-dehydroderivative is slowly oxidised to the corresponding 14β-hydroxy derivative (Rf about 0.38). The reaction mixture is filtered through Celite, and the cake is washed with ethyl acetate. The solvent is evaporated off and the residue is purified by column chromatography on silica gel (40 ml, eluent petroleum ether-ethyl acetate 7:3) to obtain 126 mg of the 13-dehydroderivative, 479 mg (46%) of the 14β-hydroxy-13-dehydroderivative and 189 mg of a mixture of both.

13-Dehydro-7-triethylsilylbaccatin III, white powder, m.p. 168° C. [α]$_D^{25}$–35 (CH$_2$Cl$_2$, C 0.67) IR (KBr) 3488, 1726, 1711, 1676, 1373, 1269, 1244, 1230, 1105 cm$^{-1}$; $^1$H-NMR (200 MH CDCl$_3$): δ 8.07 (Bz AA'), 7.60 (Bz, C), 7.49 (Bz, BB'), 6.59 (s, H-10), 5.69 (d, J=6.9 Hz, H-2), 4.92 (d, J=8.2 Hz, H-5), 4.48 (dd, J=10.6 Hz, H-7), 4.33 (d, J=8.0 Hz, H-20a), 4.12 (d, J=8.0 Hz, H-20b), 3.91, (d, J=6.9 Hz, H-3), 2.96 (d, J=20 Hz, H-14a), 2.65 (d, J=20 Hz, H-14b), 2.50 (m, H-6α), 2.23 (s, OAc), 2.19 (s, OAc+H-18), 1.67, 1.28, 1.19 (s, H-16, H-17 and H-19), 0.19 (m, TES).

13-Dehydro-14β-hydroxy-10-deacetylbaccatin III, 7,10-bistrichloroacetate: white powder, m.p. 153° C. [α]$_D^{25}$+20 (CH$_2$Cl$_2$, C 0.75) IR (KBr) 3431, 1723, 1692, 1371, 1269, 1242, 1223, 1096 cm$^{-1}$; $^1$H-NMR (500 MH CDCl$_3$): δ 8.06 (Bz AA'), 7.60 (Bz, C), 7.48 (Bz, BB'), 6.51 (s, H-10), 5.88 (d, J=6.9 Hz, H-2), 4.90 (d, J=8.2 Hz, H-5), 4.47 (dd, J=10.6 7 Hz, H-7), 4.30 (d, J=8 Hz, H-20a), 4.28 (d, J=8.2 Hz, H-20b), 4.13 (br d, J=2 Hz, H-14), 3.84 (d, J=6.9 Hz, H-3), 3.69 (br d, J=2 Hz, 14-OH), 3.62 (s, 1-OH), 2.52 (m, H-6α), 2.24 (s, OAc), 2.21 (s, OAc), 2.11 (s, H-18), 1.92 (m, H-6β), 1.74, 1.56, 1.28 (s, -h-16, H-17 and H-19), 0.94 (m, TES), 0.59 (m, TES). HRNS: 714.3092. (calculated for C$_{37}$H$_{50}$O$_{12}$Si 714.3092).

EXAMPLE IV
Oxidation/hydroxylation of 7-triethylsilylbaccatin III 10 g of activated MnO$_2$ are added to a solution of 7-triethylsilylbaccatin III (1.0 g) in acetonitrile (10 ml), with stirring at room temperature and monitoring the progress of the reaction by TLC (petroleum ether-ethyl acetate 6:4; Rf of the starting material about 0.25). After about two hours, the formation of the 13-dehydroderivative is completed (TLC analysis, Rf of the 13-dehydroderivative about 0.45). Stirring is then continued for about 188 hours, during which time further MnO$_2$ (10 g) is added. The 13-dehydroderivative is slowly oxidised to the corresponding 14β-hydroxy derivative (Rf about 0.38). The reaction mixture is filtered through Celite, and the cake is washed with ethyl acetate. The solvent is evaporated off and the residue is purified by column chromatography on silica gel (40 ml, eluent petroleum ether-ethyl acetate 7:3) to obtain 126 mg of the 13-dehydroderivative, 479 mg (46%) of the 14β-hydroxy-13-dehydroderivative and 189 mg of a mixture of both.

13-Dehydro-7-triethylsilylbaccatin III. white powder, m.p. 210° C. [α]$_D^{25}$–48 (CH$_2$Cl$_2$, C 0.50) IR (KBr) 3478, 1728, 1676, 1373, 1271, 1240, 1071, 1026 cm$^{-1}$; $^1$H-NMR (200 MH CDCl$_3$): δ 8.07 (Bz AA'), 7.64 (Bz, C), 7.50 (Bz, BB'), 6.46 (s, H-10), 5.70 (d, J=6.9 Hz, H-2), 4.95 (d, J=8.2 Hz, H-5), 4.51 (dd, J=10.7 Hz, H-7), 4.32 (d, J=8.4 Hz, H-20a), 4.14 (d, J=8.4 Hz, H-20b), 3.92, (d, J=6.9 Hz, H-3), 2.99 (d, J=20 Hz, H-14a), 2.68 (d, J=20 Hz, H-14b), 2.56 (m, H-6α), 2.29 (s, OAc), 2.18 (s, OAc), 2.08 (s, H-18), 1.68, 1.29, 1.20 (s, H-16, H-17 and H-19), 0.19.

13-Dehydro-14β-hydroxy-7-triethylsilylbaccatin III: white powder, m.p. 220° C. [α]$_D^{25}$+19 (CH$_2$Cl$_2$, C 0.42) IR (KBr) 3568, 1710, 1719, 1686, 1372, 1282, 1240, 1219, 1073 cm$^{-1}$; $^1$H-NNMR (200 MH CDCl$_3$): δ 8.09 (Bz AA'), 7.60 (Bz, C), 7.51 (Bz, BB'), 6.39 (s, H-10), 5.89 (d, J=6.9 Hz, H-2),4.94 (d, J=8.2 Hz, H-5), 4.47 (dd, J=10.7 Hz, H-7), 4.31 (br s, —H-20a+H-20b), 4.15 (s, H-14), 3.69 (d, J=6.9 Hz, H-3), 2.29 (s, OAc), 2.16 (s, H-18), 2.14 (s, OAc), 1.74, 1.21, 1.10 (s, H-16, H-17 and H-19), HRMS: 600.6112 0.19 (calculated for C$_{31}$H$_{36}$O$_{12}$Si 600.6103).

EXAMPLE V
Preparation of 1,14-carbonate-13-dehydro-7-tes-baccatin III

A solution of 13-dehydro-14β-hydroxy-7-triethylsilylbaccatin III (124 mg, 1.17 mMol) in CH$_2$Cl$_2$ (1 ml) and pyridine (0.56 ml, 6.8 mMol, 20 mol. equiv.) is added drop by drop in 5 min to a solution of phosgene (1.8 ml of a 20% solution in toluene, 3.4 mMol, 20 mol. equiv.) in CH$_2$Cl$_2$ (2 ml). The mixture is stirred at room temperature for 1 hour and subsequently the excess of phosgene is neutralised with a NaHCO$_3$ saturated solution and extracted with CH$_2$Cl$_2$. The organic phase is washed with a NaHCO$_3$ saturated solution, brine, and dried (Na$_2$SO$_4$). The solvent is evaporated off to yield a reddish residue, which is purified on a small silica gel column (about 5 ml, eluent hexane/ethyl acetate 8:2) to obtain 118 mg (92%) of the carbonate. When the reaction is carried out with triethylamine as base without the reverse addition, mixture of 1,14-carbonate and 2-debenzoyl-1,2-carbonate-14 benzoate (about 1:15) is obtained.

13-Dehydro-14β-hydroxy-7-triethylsilylbaccatin III 1,14-carbonate, white powder, m.p. 153° C. [α]$_D^{25}$+23 (CH$_2$Cl$_2$, C 0.75) IR (KBr) No. of band OH 1834, 1734, 1709, 1373, 1242, 1225, 1088, 1057 cm$^{-1}$; $^1$H-NMR (200 MH CDCl$_3$): δ 7.99 (Bz AA'), 7.60 (Bz, C), 7.48 (Bz, BB'), 6.51 (s, H-10), 6.12 (d, J=6.9 Hz, H-2), 4.90 (d, J=8.2 Hz, H-5), 4.78 (s, H-14), 4.44 (dd, J=10.7 Hz, H-7), 4.34 (d, J=8 Hz, H-20a), 4.19 (d, J=8.2 Hz, H-20b), 3.80 (d, J=6.9 Hz, H-3), 2.50 (m, H-6α), 2.23 (s, OAc), 2.22 (s, OAc), 2.19 (s, H-18), 1.92 (m, H-6β), 1.72, 1.39, 1.26 (s, —H-16, H-17 and H-19), 0.90 (m, TES), 0.56 (m, TES). HRNS: 740.2851 (calculated for C$_{38}$H$_{48}$O$_{13}$Si 740.2864).

13-Dehydro-14β-hydroxybaccatin III 1,14-carbonate, white powder 240° C. [α]$_D^{25}$–2.5 (CH$_2$Cl$_2$, C 0.4) IR (KBr) 3539, 1831, 1736, 1240, 1088, 1068, 1057, 1024 cm$^{-1}$; $^1$H-NMR (200 MH CDCl$_3$): δ 7.98 (Bz AA'), 7.61 (Bz, C), 7.50 (Bz, BB'), 6.39 (s, H-10), 6.14 (d, J=6.9 Hz, H-2), 4.98

(d, J=8.2 Hz, H-5), 4.80 (s, H-14), 4.43 (dd, J=10.7 Hz, H-7), 4.35 (d, J=8 Hz, H-20a), 4.24 (d, J=8.2 Hz, H-20b), 3.80 (d, J=6.9 Hz, H-3), 2.50 (m, H-6α), 2.30 (s, OAc), 2.20 (s, OAc), 2.15 (s, H-18), 1.90 (m, H-6β), 1.74, 1.34, 1.25 (s, H-16, H-17 and H-19), HRMS: 626.2005 (calculated for $C_{33}H_{34}O_1$ 626.1999).

EXAMPLE VI

Preparation of 1,14-carbonate-7-O-triethylsilyl baccatin III

An excess of $NaBH_4$ (about 20 mg) is added in small portions to a solution of 13-dehydro-14β-hydroxy-7-triethylsilylbaccatin III 1,14-carbonate (50 mg) in methanol (5 ml). After 30 min., the reaction mixture is added with saturated $NH_4Cl$, extracted with ethyl acetate, washed with brine, dried over $Na_2SO_4$ and the solvent is removed, to give a residue which is purified by column chromatography in silica gel (about 5 ml, elution with hexane-ethyl acetate 8:2) to obtain 35 mg of the 13α-hydroxy derivative and 9 mg of the 13β-hydroxy derivative.

14β-Hydroxy-7-triethylsilylbaccatin III 1,14-carbonate $[α]_D^{25}$–35 ($CH_2Cl_2$, C 0.60) IR (KBr) 3054, 1819, 1736, 1603, 1371, 1261, 1238, 1090, 1069, cm$^{-1}$; $^1$H-NMR (200 MH CDCl$_3$): δ 8.06 (Bz AA'), 7.65 (Bz, C), 7.50 (Bz, BB'), 6.47 (s, H-10), 6.12 (d, J=6.9 Hz, H-2), 5.05 (br d, J=5.5 Hz, H-13), 4.98 (br d, J=9 Hz, H-5), 4.83 (d, J=5 Hz, H-14), 4.50 (dd, J=10.7 Hz, H-7), 4.34 (d, J=8 Hz, H-20a), 4.23 (d, J=8 Hz, H-20b), 3.75 (d, J=6.9 Hz, H-3), 2.56 (m, H-6α) 2.34 (s, OAc), 2.22 (s, OAc), 1.78 (m, H-6β), 1.35 (s, H-18), 1.75, 1.18, 0.95 (s, —H-16, H-17 and H-19), 0.90 (m, TES), 0.62 (m, TES).

14β-Hydroxy-7-triethylsilyl-13-epibaccatin III 1,14-carbonate, amorphous $[α]_D^{25}$–13 ($CH_2Cl_2$, C 0.60) IR (KBr) 3630, 1825, 1734, 1603, 1375, 1262, 1091, 1071, 1049 cm$^{-1}$; $^1$H-NMR (200 MH CDCl$_3$): δ 8.01 (Bz AA'), 7.63 (Bz, C), 7.48 (Bz, BB'), 6.44 (s, H-10), 6.12 (d, J=7.2 Hz, H-2), 4.90 (br d, J=9 Hz, H-5), 4.81 (d, J=8 Hz, H-14), 4.48 (br, J=8, H-13), 4.50 (dd, J=10, 7 Hz, H-7), 4.41 (d, J=8 Hz, H-20a), 4.31 (d, J=8 Hz, H-20b), 3.68 (d, J=7.2 Hz, H-3), 2.60 (m, H-6α), 2.32 (s, OAc), 2.26 (s, H-18), 2.21 (s, OAc), 1.80 (m, H-6β), 1.72, 1.43, 1.27 (s, —H-16, H-17 and H-19), 0.93 (m, TES), 0.61 (m, TES).

EXAMPLE VII

Preparation of 13-dehydro-14β-hydroxyl-7,10-bistrichloroacetyl-baccatin III 1,14-carbonate A solution of 13-dehydro-14β-hydroxy-7,10-bistrichloroacetyl-baccatin III (200 mg) in $CH_2Cl_2$ (2 ml) and pyridine (1.12 ml, 20 equiv.) is added in 5 min with a solution of phosgene (20% in toluene, 3.6 ml, 20 equiv.) in $CH_2Cl_2$ (2 ml). The mixture is stirred at r.t. for 1 h, then the excess of phosgene is neutralised with a $NaHCO_3$ saturated solution (3 ml). The mixture is extracted with $CH_2Cl_2$, the organic phase is washed with a $NaHCO_3$ saturated solution, then with a NaCl saturated solution and dried over $Na_2SO_4$. After removal of the solvent, the residue is purified by chromatography on a silica gel column (eluent hexane/AcOEt 9:1) to obtain 175 mg (89%) of the carbonate.

13-Dehydro-14β-hydroxy-7,10-bistrichloroacetyl-baccatin III 1,14-carbonate, amorphous white solid. IR (KBr) 1834, 1771, 1735, 1709, 1232, 1103, 1010, 854 cm$^{-1}$.

$^1$H NMR (200 MHz, CDCl$_3$): δ=8.03 (Bz AA'), 7.60 (Bz, C), 7.50 (Bz, BB'), 6.52 (s, H-10), 5.92 (d, J=6.7 Hz, H-2), 5.70 (br t, J=8.0 Hz, H-7), 4.95 (br d, J=8.2 Hz, H-20b), 4.77 (s, H-14), 4.02 (d, J=6.7 Hz, H-3), 2.71 (m, H-6), 2.29 (s, OAc), 1.96 (s, H-18), 1.27-1.01 (m, H-16, H-17, H-19).

EXAMPLE VIII

Preparation of 14β-hydroxy-10-deacetylbaccatin III 1,14-carbonate

A solution of 13-dehydro-14β-hydroxy-7,10-bistrichloroacetyl-baccatin III 1,14-carbonate (500 mg) in MeOH (8 ml) is cooled to 0° C. on ice bath and added with solid $NaBH_4$ (44 mg) in 5 min. The mixture is stirred at r.t. for 1 h, then cooled to 0° C. Acetone is added (2 ml) in 5 min, the mixture is concentrated, then added with AcOEt (10 ml) and filtered through Celite. The clear solution is washed with a NaCl saturated solution and dried over $Na_2SO_4$. The solvent is evaporated off to give a residue (4.5:1 mixture of C13 epimers) which is purified by chromatography on a silica gel column (eluent hexane/AcOEt 1:1) to obtain 251 mg of the 13β epimer and 55 mg of the 13α epimer (88% total) of the deprotected carbonate.

13α-14β-hydroxy-10-deacetylbaccatin III 1,14-carbonate amorphous white solid. IR (KBr): 3520 (OH), 1834, 1709, 1232, 1103, 1010, 854 cm$^{-1}$.

$^1$H NMR (200 MHz, CDCl$_3$): δ 8.03 (Bz AA'), 7.60 (Bz, C), 7.50 (Bz, BB'), 6.27 (s, H-10), 5.92 (d, J=6.7 Hz, H-2), 4.95 (br d, J=8.2 Hz, H-20b), 4.85 (m, H-13), 4.77 (s, H-14), 4.42 (br t, J=8.0 Hz, H-7), 4.02 (d, J=6.7 Hz, H-3), 2.71 (m, H-6), 2.29 (s, OAc), 1.96 (s, H-18), 1.27-1.01 (m, H-16, H-17, H-19).

13α-14β-hydroxy-10-deacetylbaccatin III 1,14-carbonate, amorphous white solid. IR (KBr): 3520 (OH), 1834, 1709, 1232, 1103, 1010, 854 cm$^{-1}$.

$^1$H NMR (200 MHz, CDCl$_3$): δ=8.03 (Bz AA'), 7.60 (Bz, C), 7.50 (Bz, BB'), 6.27 (s, H-10), 5.92 (d, J=6.7 Hz, H-2), 4.95 (br d, J=8.2 Hz, H-20b), 4.80 (m, H-13), 4.77 (s, H-14), 4.42 (br t, J=8.0 Hz, H-7), 4.02 (d, J=6.7 Hz, H-3), 2.71 (m, H-6), 2.29 (s, OAc), 1.96 (s, H-18), 1.27-1.01 (m, H-16, H-17, H-19).

What is claimed is:

1. A process for the preparation of 14β-hydroxy-1,14-carbonate-deacetylbaccatin III, which comprises the following steps:

a. protection of the hydroxyls at the 7- and 10-positions of 10-deacetylbaccatin III:

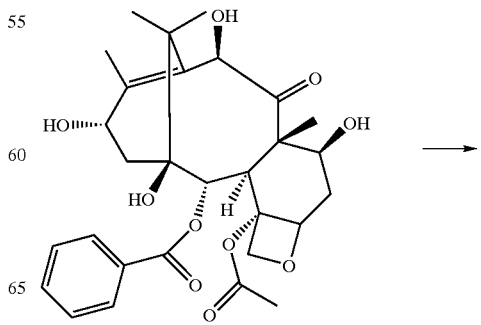

-continued

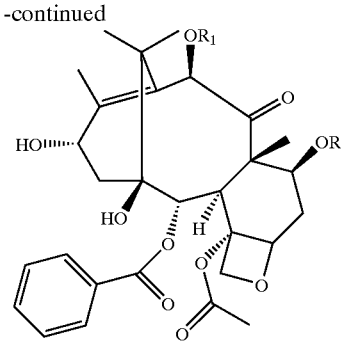

wherein R and $R_1$ are selected from hydrogen, $C_1$–$C_{10}$ alkyl or aryl, $C_1$–$C_{10}$ alkyl- or aryl-carbonyl, trichloroacetyl, $C_1$–$C_4$ trialkylsilyl; preferably, when R and $R_1$ are the same, they are trichloroacetyl, whereas when they are different, preferably R is trichloroacetyl and $R_1$ is acetyl, or R is triethyl or trimethylsilyl and $R_1$ is acetyl;

b. two-step oxidation to give the derivative oxidised to carbonyl at the 13-position and hydroxylated at the 14-position:

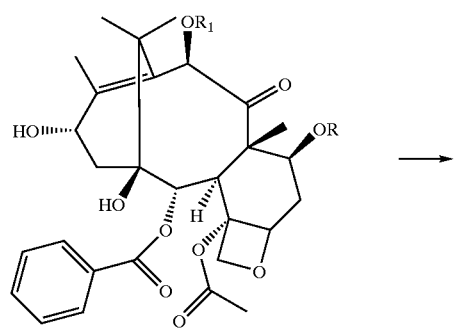

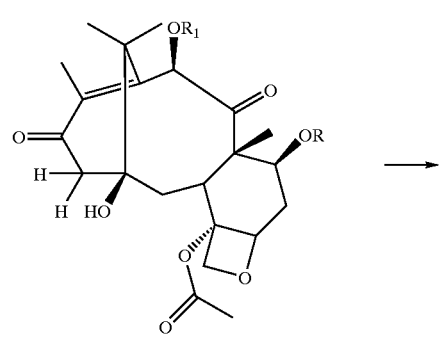

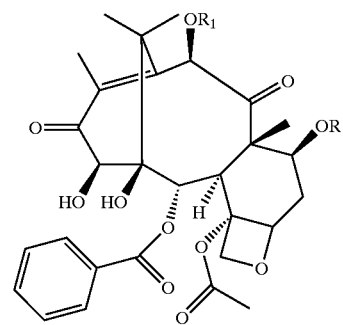

c. carbonation of the vicinal hydroxyls at the 1- and 14-positions to give the 1,14-carbonate derivative:

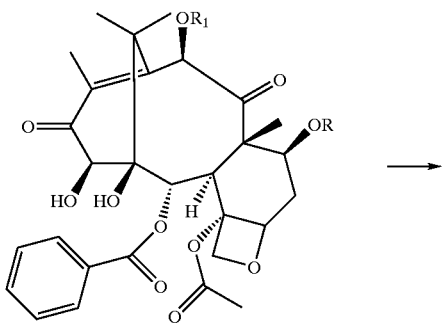

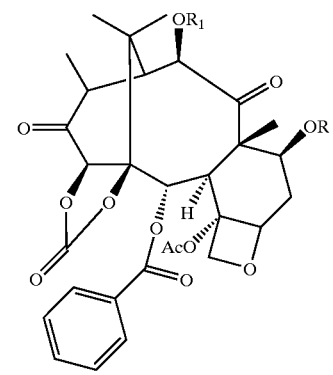

d. reduction of the carbonyl at the 13-position:

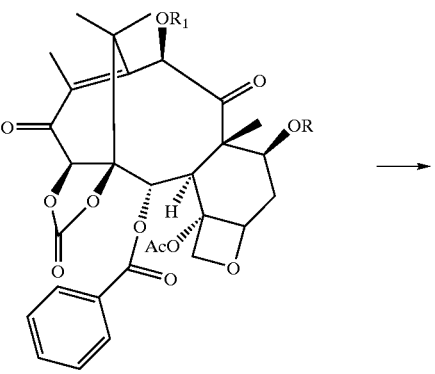

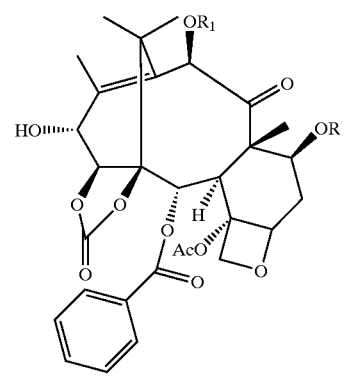

e. removal of the protective groups at the 7- and 10-positions:

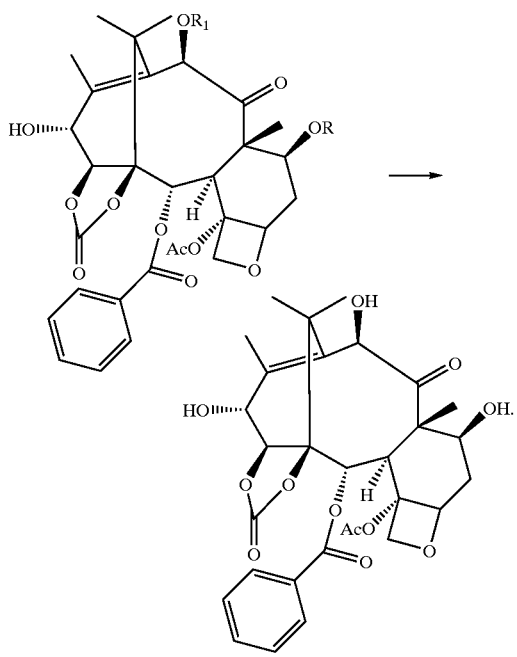

2. A process as claimed in claim 1 wherein R and $R_1$ are the same and are trichloroacetyl, or R and $R_1$ are different and then R is trichloroacetyl and $R_1$ is acetyl, or R is triethyl or trimethylsilyl and $R_1$ is acetyl.

3. A process as claimed in claim 2, in which R and $R_1$ are trichloroacetyl.

4. A process as claimed in claim 3, in which the protection step of the hydroxyls at the 7- and 10-positions is carried out with trichloroacetyl chloride in methylene chloride in the presence of triethylamine and of catalytic amounts of N,N-dimethylaminopyridine.

5. A process as claimed in claim 1, in which the oxidation of the hydroxyl at the 13-position and the hydroxylation at the 14-position are effected with manganese dioxide or bismuth dioxide in a solvent selected from acetontrile, acetone or ethyl acetate/methylene chloride mixtures.

6. A process as claimed in claim 1, in which the carbonation step of the hydroxyls at the 1- and 14-positions is effected with phosgene in methylene chloride/toluene mixture in the presence of pyridine.

7. A process as claimed in claim 1, in which the reduction step to 13-hydroxy is effected with sodium borohydride in methanol.

* * * * *